(12) United States Patent
Nag et al.

(10) Patent No.: US 11,804,295 B2
(45) Date of Patent: Oct. 31, 2023

(54) MACHINE LEARNING BASED SAFETY CONTROLLER

(71) Applicant: CareFusion 303, Inc., San Diego, CA (US)

(72) Inventors: Abhikesh Nag, San Diego, CA (US); Cynthia Yamaga, Oceanside, CA (US)

(73) Assignee: CareFusion 303, Inc., San Diego, CA (US)

( * ) Notice: Subject to any disclaimer, the term of this patent is extended or adjusted under 35 U.S.C. 154(b) by 116 days.

(21) Appl. No.: 16/736,656

(22) Filed: Jan. 7, 2020

(65) Prior Publication Data

US 2020/0219611 A1 Jul. 9, 2020

Related U.S. Application Data

(60) Provisional application No. 62/789,337, filed on Jan. 7, 2019.

(51) Int. Cl.
*G16H 40/20* (2018.01)
*G16H 10/60* (2018.01)
(Continued)

(52) U.S. Cl.
CPC .............. *G16H 40/20* (2018.01); *G06F 17/18* (2013.01); *G06N 20/00* (2019.01); *G16H 10/60* (2018.01); *G16H 20/13* (2018.01)

(58) Field of Classification Search
CPC ........ G16H 40/20; G16H 10/60; G16H 20/13; G06F 17/18; G06N 20/00
(Continued)

(56) References Cited

U.S. PATENT DOCUMENTS 5,945,651 A   8/1999   Chorosinski et al.
6,650,964 B2  11/2003  Spano, Jr. et al.
(Continued)

FOREIGN PATENT DOCUMENTS

AU   2017 279 693 A1   1/2018
CA       2636115 C       6/2014
(Continued)

OTHER PUBLICATIONS

Benjamin, X.C. et al. (2012). "Visual identification of medicine boxes using features matching." *IEEE International Conference on Virtual Environments Human-Computer Interfaces and Measurement Systems (VECIMS) Proceedings*, 43-47. Doi: 10.1109/VECIMS.2012.6273190.

(Continued)

*Primary Examiner* — Jonathan Ng
*Assistant Examiner* — Benjamin L. Hanks
(74) *Attorney, Agent, or Firm* — Mintz Levin Cohn Ferris Glovsky and Popeo, P.C.

(57) ABSTRACT

A method may include identifying a shift associated with a clinician by applying a machine learning model trained to identify, based on a series of transaction records associated with the clinician, one or more shifts associated with the clinician. The clinician may be identified as likely to engage in a hazardous behavior based at least on the shift associated with the clinician. In response to determining that the clinician as likely to engage in the hazardous behavior, activating a protective workflow. The protective workflow may be configured to prevent the clinician from engaging in the hazardous behavior as well as to collect evidence associated with the hazardous behavior. Related methods and articles of manufacture are also disclosed.

20 Claims, 6 Drawing Sheets

(51) Int. Cl.
  *G16H 20/13* (2018.01)
  *G06N 20/00* (2019.01)
  *G06F 17/18* (2006.01)
(58) Field of Classification Search
  USPC ........................................................ 705/2–3
  See application file for complete search history.

(56) References Cited

U.S. PATENT DOCUMENTS

| | | | |
|---|---|---|---|
| 6,671,579 | B2 | 12/2003 | Spano, Jr. et al. |
| 6,842,736 | B1 | 1/2005 | Brzozowski |
| 6,868,344 | B1 | 3/2005 | Nelson |
| 7,119,689 | B2 | 10/2006 | Mallett et al. |
| 7,184,897 | B2 | 2/2007 | Nelson |
| 7,275,645 | B2 | 10/2007 | Mallett et al. |
| 7,303,081 | B2 | 12/2007 | Mallett et al. |
| 7,311,207 | B2 | 12/2007 | Mallett et al. |
| 7,318,529 | B2 | 1/2008 | Mallett et al. |
| 7,562,025 | B2 | 7/2009 | Mallett et al. |
| 8,147,479 | B1 | 4/2012 | Wach et al. |
| 8,195,328 | B2 | 6/2012 | Mallett et al. |
| 8,280,550 | B2 | 10/2012 | Levy et al. |
| 8,319,669 | B2 | 11/2012 | Weller |
| 8,357,114 | B2 | 1/2013 | Poutiatine et al. |
| 8,595,021 | B2 | 11/2013 | Mallett et al. |
| 8,606,596 | B1 | 12/2013 | Bochenko et al. |
| 8,725,532 | B1 | 5/2014 | Ringold |
| 8,738,177 | B2 | 5/2014 | van Ooyen et al. |
| 8,768,724 | B2 | 7/2014 | Whiddon et al. |
| 8,905,964 | B2 | 12/2014 | Poutiatine et al. |
| 9,158,892 | B2 | 10/2015 | Levy et al. |
| 9,202,052 | B1 | 12/2015 | Fang et al. |
| 9,227,025 | B2 | 1/2016 | Butterfield et al. |
| 9,354,178 | B2 | 5/2016 | Lee |
| 9,427,520 | B2 | 8/2016 | Batch et al. |
| 9,456,958 | B2 | 10/2016 | Reddy et al. |
| 9,523,635 | B2 | 12/2016 | Tilden |
| 9,636,273 | B1 | 5/2017 | Harris |
| 9,752,935 | B2 | 9/2017 | Marquardt et al. |
| 9,796,526 | B2 | 10/2017 | Smith et al. |
| 9,817,850 | B2 | 11/2017 | Dubbels et al. |
| 9,836,485 | B2 | 12/2017 | Dubbels et al. |
| 9,842,196 | B2 | 12/2017 | Utech et al. |
| 9,881,129 | B1 | 1/2018 | Cave |
| 9,958,324 | B1 | 5/2018 | Marquardt et al. |
| 10,032,344 | B2 | 7/2018 | Nelson et al. |
| 10,101,269 | B2 | 10/2018 | Judge et al. |
| 10,187,288 | B2 | 1/2019 | Parker et al. |
| 10,209,176 | B2 | 2/2019 | Proskurowski et al. |
| 10,241,038 | B2 | 3/2019 | Nishimura et al. |
| 10,249,153 | B2 | 4/2019 | Nelson et al. |
| 10,309,832 | B2 | 6/2019 | Marquardt et al. |
| 10,345,242 | B2 | 7/2019 | Zhao et al. |
| 10,832,207 | B2 | 11/2020 | Vahlberg et al. |
| 11,037,666 | B1* | 6/2021 | Benoit .................... H04L 41/16 |
| 11,116,892 | B2 | 9/2021 | Brady et al. |
| 11,147,914 | B2 | 10/2021 | Estes |
| 2003/0158751 | A1 | 8/2003 | Suresh et al. |
| 2008/0059226 | A1 | 3/2008 | Melker et al. |
| 2008/0082360 | A1 | 4/2008 | Bailey et al. |
| 2008/0140715 | A1 | 6/2008 | Hakos |
| 2008/0288430 | A1 | 11/2008 | Friedlander et al. |
| 2008/0306796 | A1 | 12/2008 | Zimmerman et al. |
| 2008/0319795 | A1 | 12/2008 | Poteet et al. |
| 2009/0083231 | A1 | 3/2009 | Eberholst et al. |
| 2009/0160646 | A1 | 6/2009 | Mackenzie et al. |
| 2011/0016110 | A1 | 1/2011 | Egi et al. |
| 2011/0161108 | A1* | 6/2011 | Miller ................. G06Q 30/0185 |
| | | | 705/3 |
| 2012/0226447 | A1 | 9/2012 | Nelson et al. |
| 2012/0265336 | A1 | 10/2012 | Mallett et al. |
| 2012/0325330 | A1 | 12/2012 | Prince et al. |
| 2013/0002429 | A1 | 1/2013 | Johnson |
| 2013/0018356 | A1 | 1/2013 | Prince et al. |
| 2013/0070090 | A1 | 3/2013 | Bufalini et al. |
| 2013/0144254 | A1 | 6/2013 | Amirouche et al. |
| 2013/0253700 | A1 | 9/2013 | Carson et al. |
| 2013/0282392 | A1 | 10/2013 | Wurm |
| 2013/0325727 | A1 | 12/2013 | MacDonell et al. |
| 2014/0074284 | A1 | 3/2014 | Czaplewski et al. |
| 2014/0081652 | A1 | 3/2014 | Klindworth |
| 2014/0149131 | A1 | 5/2014 | Bear et al. |
| 2014/0249776 | A1 | 9/2014 | King et al. |
| 2014/0277707 | A1 | 9/2014 | Akdogan et al. |
| 2014/0375324 | A1 | 12/2014 | Matsiev et al. |
| 2015/0038898 | A1 | 2/2015 | Palmer et al. |
| 2015/0081324 | A1 | 3/2015 | Adjaoute |
| 2015/0109437 | A1 | 4/2015 | Yang et al. |
| 2015/0272825 | A1 | 10/2015 | Lim et al. |
| 2015/0286783 | A1 | 10/2015 | Kumar et al. |
| 2015/0323369 | A1 | 11/2015 | Marquardt |
| 2015/0339456 | A1 | 11/2015 | Sprintz |
| 2015/0362350 | A1 | 12/2015 | Miller et al. |
| 2016/0034274 | A1 | 2/2016 | Diao et al. |
| 2016/0062371 | A1 | 3/2016 | Davidian et al. |
| 2016/0161705 | A1 | 6/2016 | Marquardt et al. |
| 2016/0166766 | A1 | 6/2016 | Schuster et al. |
| 2016/0283691 | A1 | 9/2016 | Ali |
| 2017/0017760 | A1 | 1/2017 | Freese et al. |
| 2017/0032102 | A1 | 2/2017 | Skoda |
| 2017/0076065 | A1 | 3/2017 | Darr et al. |
| 2017/0083681 | A1 | 3/2017 | Sprintz et al. |
| 2017/0103203 | A1 | 4/2017 | Sharma et al. |
| 2017/0108480 | A1 | 4/2017 | Clark et al. |
| 2017/0109480 | A1* | 4/2017 | Vahlberg ................ G16H 40/20 |
| 2017/0109497 | A1 | 4/2017 | Tribble et al. |
| 2017/0120035 | A1 | 5/2017 | Butterfield et al. |
| 2018/0028408 | A1 | 2/2018 | Li et al. |
| 2018/0039736 | A1 | 2/2018 | Williams |
| 2018/0046651 | A1 | 2/2018 | Dubbels et al. |
| 2018/0157803 | A1 | 6/2018 | Mirov |
| 2018/0192942 | A1 | 7/2018 | Clark et al. |
| 2018/0231415 | A1 | 8/2018 | Marquardt et al. |
| 2018/0247703 | A1 | 8/2018 | D'Amato |
| 2018/0259446 | A1 | 9/2018 | Coffey et al. |
| 2018/0299375 | A1 | 10/2018 | Young et al. |
| 2018/0330824 | A1* | 11/2018 | Athey ..................... G16B 40/20 |
| 2018/0365386 | A1* | 12/2018 | Vanderveen ........... G06Q 50/00 |
| 2019/0088354 | A1 | 3/2019 | Yanowitz et al. |
| 2019/0117883 | A1 | 4/2019 | Abrams et al. |
| 2019/0124118 | A1 | 4/2019 | Swafford |
| 2019/0180862 | A1 | 6/2019 | Wisser et al. |
| 2019/0244699 | A1 | 8/2019 | Loebig et al. |
| 2019/0247703 | A1 | 8/2019 | Welde et al. |
| 2019/0341142 | A1 | 11/2019 | Nag et al. |
| 2019/0355461 | A1* | 11/2019 | Kumar ................... G16H 10/60 |
| 2020/0085686 | A1 | 3/2020 | Aliakbarian et al. |
| 2020/0098474 | A1 | 3/2020 | Vanderveen |
| 2020/0222627 | A1 | 7/2020 | Guerra et al. |
| 2020/0230316 | A1 | 7/2020 | Guerra et al. |
| 2021/0133201 | A1 | 5/2021 | Tribble et al. |
| 2021/0308385 | A1 | 10/2021 | Nisha et al. |
| 2022/0093239 | A1 | 3/2022 | Nag et al. |

FOREIGN PATENT DOCUMENTS

| | | |
|---|---|---|
| CA | 2848274 C | 9/2016 |
| EP | 1 973 593 B1 | 4/2013 |
| EP | 1 593 076 B1 | 10/2019 |
| WO | WO-2006/034367 A2 | 3/2006 |
| WO | WO-2014/055925 A1 | 4/2014 |
| WO | WO-2015/187682 A1 | 12/2015 |
| WO | WO-2019/028004 A1 | 2/2019 |
| WO | WO-2019/031331 A1 | 2/2019 |

OTHER PUBLICATIONS

Cakaloglu, T. (Nov. 1, 2017). "Medi-Deep: Deep control in a medication usage." *2017 IEEE International Conference of Bioinfomratice and Biomedicine (BIBM)*, 899-904. Doi: 10.1109/BIBM.2017.8217776.

(56) References Cited

OTHER PUBLICATIONS

Neuman, M.R. et al. (May 13, 2012), "Advances in Medical Devices and Medical Electronics," in Proceedings of the IEEE, vol. 100, No. Special Centennial Issue, pp. 1537-1550, doi: 10.1109/JPROC.2012.2190684.

Shishvan, O. Rajabi et al. (2018). "Machine Intelligence in Healthcare and Medical Cyber Physical Systems: A Survey." *IEEE Access*. vol. 6, 46419-46494. doi: 10.1109/ACCESS.2018.2866049.

Uniyal, D. et al. (Nov. 7, 2014), "Pervasive Healthcare—A Comprehensive Survey of Tools and Techniques," arXiv:1411.1821v1, 48 pages.

Yaniv, Z. et al. (Oct. 1, 2016). "The National Library of Medicine Pill Image Recognition Challenge: An Initial Report." *Oct. 2016 IEEE Applied Imagery Pattern Recognition Workshop, (AIPR)*, 1-9. Doi: 10.1109/AIPR.2016.8010584.

Zhan, A. et al. (Jan. 5, 2016) "High Frequency Remote Monitoring of Parkinson's Disease via Smartphone: Platform Overview and Medication Response Detection," Retrieved Apr. 29, 2021. 12 pages.

Qui et al. (2016). "A survey of machine learning for big data processing." *EURASIP Journal on Advances in Signal Processing*, Article No. 67, 16 pages.

Yang, J., McAuley, J.J., & Leskovec, J. (2013). "Community Detection in Networks with Node Attributes." *2013 IEEE 13th International Conference on Data Mining*, 1151-1156.

\* cited by examiner

MACHINE LEARNING BASED SAFETY CONTROLLER

CROSS REFERENCE TO RELATED APPLICATION

This application claims priority to U.S. Provisional Application No. 62/789,337, entitled "MACHINE LEARNING BASED SHIFT TRACKING" and filed on Jan. 7, 2019, the disclosure of which is incorporated herein by reference in its entirety.

TECHNICAL FIELD

The subject matter described herein relates generally to machine learning and more specifically to a machine learning based technique for detecting and preventing hazardous behavior.

BACKGROUND

Hazardous behavior may arise in a variety of medical settings to result in resource losses and harm to patients as well as clinicians. Diversion may be one example of hazardous behavior in which a clinician keeps a substance for unauthorized personal use and/or personal gain instead of administering the substance to a patient and/or wasting the substance. High-value medical supplies and controlled medications (e.g., opiates, opioids, narcotics, and/or the like) may be especially prone to diversion. Other examples of hazardous behavior may include the unintentional mishandling of substances. For instance, a clinician may retrieve, administer, and/or waste an incorrect type and/or quantity of a medication.

SUMMARY

Systems, methods, and articles of manufacture, including computer program products, are provided for a machine learning based safety controller. In some example embodiments, there is provided a system that includes at least one processor and at least one memory. The at least one memory may include program code that provides operations when executed by the at least one processor. The operations may include: identifying a first shift associated with a first clinician by at least applying a machine learning model trained to identify, based at least on a series of transaction records associated with the first clinician, one or more shifts associated with the first clinician; determining, based at least on the first shift associated with the first clinician, that the first clinician is likely to engage in a hazardous behavior; and in response to determining that the first clinician is likely to engage in the hazardous behavior, activating a protective workflow.

In some variations, one or more features disclosed herein including the following features can optionally be included in any feasible combination. The first shift associated with the first clinician may be compared to a second shift associated with the first clinician and/or a third shift associated with a second clinician. The first clinician may be determined as likely to engage in the hazardous behavior based at least on the comparing.

In some variations, the first shift associated with the first clinician may be compared to the second shift associated with the first clinician and/or the third shift associated with the second clinician by at least comparing a first plurality of transaction records included in the first shift to a second plurality of transaction records included in the second shift and/or the third shift. The first clinician may be determined to be likely to engage in the hazardous behavior in response to detecting one or more anomalous transaction records included in the first plurality of transaction records.

In some variations, the first shift associated with the first clinician may be compared to the second shift associated with the first clinician and/or the third shift associated with the second clinician based at least on the first shift having one or more attributes in common with the second shift and/or the third shift.

In some variations, the first shift associated with the first clinician may be compared to the third shift associated with the second clinician based at least on the first clinician and the second clinician having one or more attributes in common.

In some variations, one or more high risk periods during which the first clinician is likely to engage in the hazardous behavior may be identified based at least on the first shift associated with the first clinician. The protective workflow may be activated during the one or more high risk periods.

In some variations, the one or more high risk periods may include at least one of a first quantity of time subsequent to a start of the first shift and a second quantity of time prior to an end of the first shift.

In some variations, the one or more high risk periods may include a portion of the first shift exceeding a threshold quantity of time.

In some variations, the machine learning model may include a probabilistic machine learning model. The probabilistic machine learning model may be trained to determine, based at least on the series of transaction records associated with the first clinician, a probability of the first clinician being in an on-duty state and in an off-duty state.

In some variations, a first transition from the off-duty state to the on-duty state may correspond to a start of the first shift associated with the first clinician. A second transition from the on-duty state to the off-duty state may correspond to an end of the first shirt associated with the first clinician.

In some variations, the probabilistic machine learning model may be trained using a reinforcement learning technique comprising Q-learning, Monte Carlo, state-action-reward-state-action (SARSA), deep Q network (DQN), deep deterministic policy gradient (DDPG), asynchronous actor-critic algorithm (A3C), trust region policy optimization (TRPO), and/or proximal policy optimization (PPO).

In some variations, the series of transaction records may include one or more transaction records generated in response to the first clinician interacting with an access control system. A transaction record may indicate scanning, via the access control system, an access badge at an entry point of a treatment facility.

In some variations, the series of transaction records may include one or more transaction records generated in response to the first clinician interacting with a dispensing system. A transaction record may indicate accessing a dispensing cabinet associated with the dispensing system to retrieve a substance.

In some variations, the series of transaction records may include one or more transaction records generated in response to the first clinician interacting with an electronic medical record (EMR) system. A transaction record may indicate administration of a substance to a patient identified in the EMR system.

In some variations, the protective workflow may include generating an alert identifying the first clinician as likely to engage in the hazardous behavior.

In some variations, the protective workflow may include activating one or more surveillance devices in response to the first clinician interacting with a medical device and/or isolating substances accessed by the first clinician.

In some variations, the protective workflow may include configuring one or more medical devices to prevent the first clinician from retrieving, administering, and/or wasting a substance without authorization from a second clinician.

In another aspect, there is provided a method for machine learning based safety controls. The method may include: identifying a shift associated with a clinician by at least applying a machine learning model trained to identify, based at least on a series of transaction records associated with the clinician, one or more shifts associated with the clinician; determining, based at least on the shift associated with the clinician, that the clinician is likely to engage in a hazardous behavior; and in response to determining that the clinician is likely to engage in the hazardous behavior, activating a protective workflow.

In another aspect, there is provided a computer program product that includes a non-transitory computer readable medium storing instructions. The instructions may cause operations when executed by at least one data processor. The operations may include: identifying a shift associated with a clinician by at least applying a machine learning model trained to identify, based at least on a series of transaction records associated with the clinician, one or more shifts associated with the clinician; determining, based at least on the shift associated with the clinician, that the clinician is likely to engage in a hazardous behavior; and in response to determining that the clinician is likely to engage in the hazardous behavior, activating a protective workflow.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to applying a machine learning model to detect and prevent hazardous behavior, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
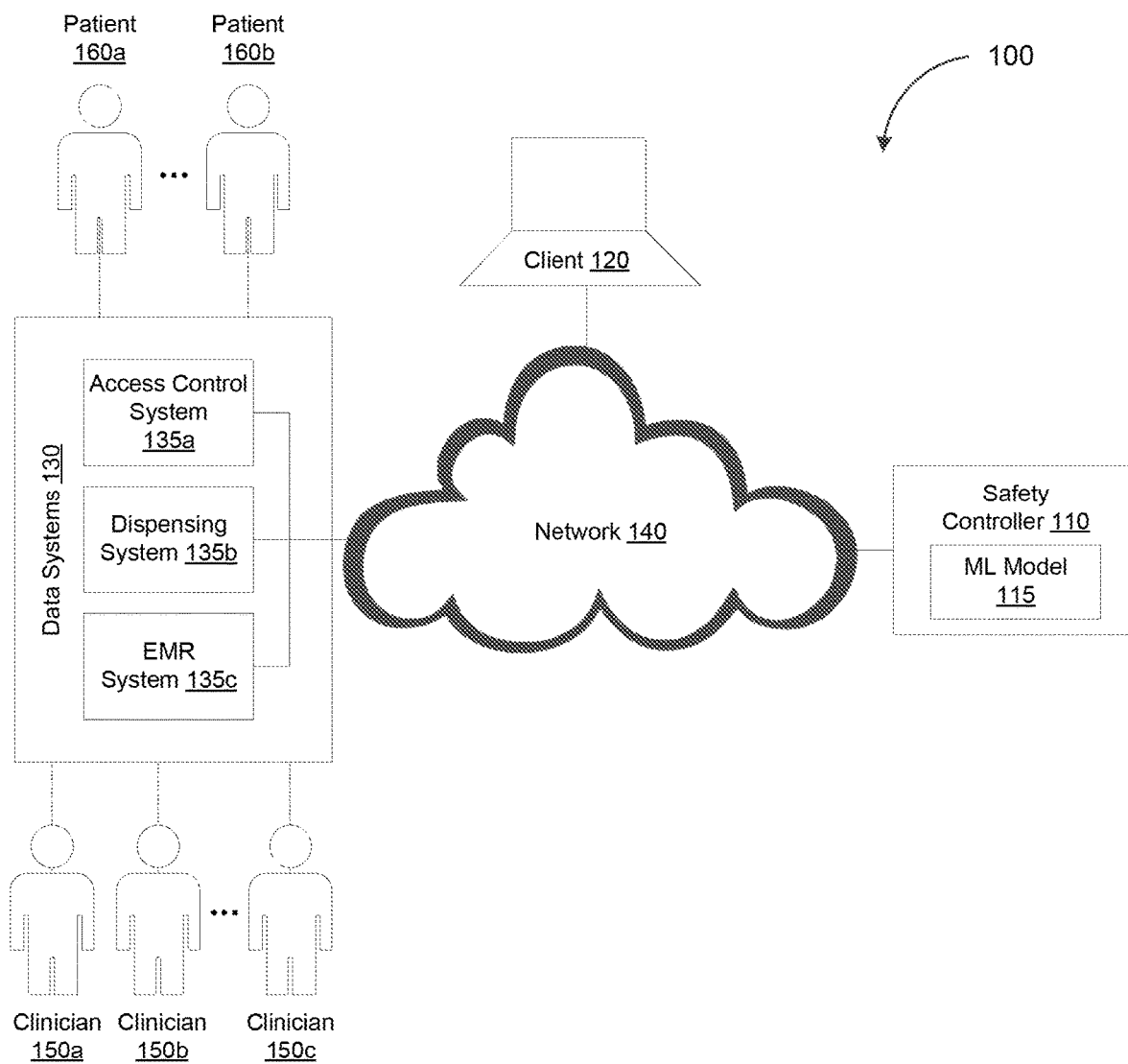
FIG. 1 depicts a system diagram illustrating an example of a safety control system, in accordance with some example embodiments.

Hazardous behavior may occur at various times in a medical facility. For example, medical supplies and medications may be susceptible to diversion and/or unintentional mishandling at any point during the shipping, receiving, stocking, dispensing, administration, and/or wasting of the substance. Prescription pain medications may be especially prone to diversion and unintentional mishandling due to a lack sufficient custodial oversight during the shipping, receiving, stocking, dispensing, administration, and wasting of the prescription pain medication. For example, dispensing cabinets at the medical facility may be accessible to multiple clinicians. Moreover, different clinicians may be responsible for the dispensing, administration, and wasting of the medication. Consequently, hazardous behavior is typically detected after the fact, when the hazardous behavior has already resulted in loss and/or injury. Delayed detection of hazardous behavior may further prevent the identification of the clinicians responsible for the hazardous behavior.

In some example embodiments, a safety controller may be configured to detect and prevent hazardous behavior including by analyzing transactional data representative of the activities of various clinicians. For example, the safety controller may apply a machine learning model trained to identify, based at least on a series of transaction data associated with a clinician, one or more shifts for the clinician. Moreover, the safety controller may identify, based at least on the one or more shifts associated with the clinician, one or more high risk periods during which the clinician is likely to engage in hazardous behavior including, for example, shift changes, portions of shifts exceeding a threshold quantity of time, and/or the like. In response to identifying the one or more high risk periods, the safety controller may activate a protective workflow configured to prevent the clinician from engaging in hazardous behavior during the high risk periods as well as to collect evidence associated with the hazardous behavior.

In some example embodiments, the safety controller may also be configured to identify a first clinician as likely to engage in hazardous behavior by comparing a first shift associated with the first clinician to at least a second shift associated with the first clinician and/or a third shift associated with a second clinician. The safety controller may detect, based at least on the comparison, anomalies indicative of the first clinician as having engaged in hazardous behavior such as, for example, the diversion and/or mishandling of a substance. In response to detecting the hazardous behavior, the safety controller may activate a protective workflow configured to prevent the clinician from continuing to engage in the hazardous behavior during the high risk periods as well as to collect evidence associated with the hazardous behavior.

In some example embodiments, the protective workflow may include the safety controller generating and sending an alert. An alert may cause a device to adjust one or more functions. For example, an alert may cause the device to present a human perceivable indication (e.g., visual, tactile, auditory messaging) such as via a user interface, a haptic motor, or an audio speaker/amplifier. As another example, an alert may alter operations available for activation via the device or cause a reconfiguration of device circuitry to change mode of operation (e.g., locked/unlocked, power off, etc.). The alert may identify the clinician who is likely to engage in hazardous behavior such as, for example, diversion and/or mishandling of a substance. Alternatively and/or additionally, the protective workflow may include limiting and/or preventing the clinician from performing certain activities (e.g., retrieving, administering, and/or wasting certain substances), for example, during certain high risk periods (e.g., shift changes, portions of shifts exceeding a threshold quantity of time, and/or the like). The protective workflow may also include the safety controller activating one or more surveillance devices (e.g., video cameras, still image cameras, audio recorders, and/or the like) at a medical device (e.g., dispensing cabinet, infusion pump, wasting station, and/or the like) whenever the clinician accesses the medical device. The protective workflow may further include the safety controller configuring a medical management device to isolate the substance accessed by the clinician.

FIG. 1 depicts a system diagram illustrating an example of a safety control system 100, in accordance with some example embodiments. Referring to FIG. 1, the safety system 100 may include a safety controller 110, a client 120, and one or more data systems 130. As FIG. 1 shows, the safety controller 110, the client 120, and the one or more data systems 130 may be communicatively coupled via a network 140. For example, the safety controller 110 may be accessible to the client 120 as a cloud-based service (e.g., a software-as-a-service (SaaS) and/or the like). Alternatively, the safety controller 110 may be at least partially embedded and/or implemented within the one or more data systems such as, for example, at an access control system 135a, a dispensing system 135b, an electronic medical record (EMR) system 135c, and/or the like. That is, the safety controller 110 may be at least partially embedded and/or implemented within a medical device such as, for example, a dispensing cabinet, an infusion pump, a wasting station, and/or the like. Accordingly, at least some functionalities of the safety controller 110 may be accessed via the one or more data systems 130. Moreover, the safety controller 110 may be updated and/or configured as part of servicing and/or updating the corresponding data systems 130. The client 120 may be a processor-based device including, for example, a smartphone, a tablet computer, a wearable apparatus, a desktop computer, a laptop computer, a workstation, and/or the like. Meanwhile, the network 140 may be any wired and/or wireless network including, for example, a public land mobile network (PLMN), a local area network (LAN), a virtual local area network (VLAN), a wide area network (WAN), the Internet, and/or the like.

In some example embodiments, the safety controller 110 may be configured to identify shifts associated with one or more clinicians including, for example, a first clinician 150a, a second clinician 150b, and/or the like. For example, the safety controller 110 may identify shifts associated with each of the first clinician 150a and the second clinician 150b based on transaction records from one or more data systems 130. Referring again to FIG. 1, the data systems 130 may include the access control system 135a, the dispensing system 135b, and the electronic medical record (EMR) system 135c. While treating a first patient 160a and/or a second patient 160b, the first clinician 150a and/or the second clinician 150b may interact with the data systems 130 and trigger the generation of one or more corresponding transaction records. The safety controller 110 may apply, to at least a portion of the transaction records generated by the data systems 130, a machine learning model 115 trained to identify at least a first shift associated with the first clinician 150a and/or a second shift associated with the second clinician 150b.

For example, the first clinician 150a interacting with the access control system 135a, for example, by scanning an access badge at an entry point in a treatment facility, may trigger the generation of a first transaction record that includes at least an identifier of the first clinician 150a and a timestamp indicating when the first clinician 150a interacted with the access control system 135a. The first clinician 150a dispensing a substance for the first patient 160a from a dispensing cabinet may trigger the generation of a second transaction record that includes a timestamp, a clinician identifier of the first clinician 150a, a device identifier of the dispensing cabinet, a patient identifier of the first patient 160a, an identifier of the substance retrieved from the dispensing cabinet, a quantity of the substance retrieved from the substance cabinet, and/or the like.

Alternatively and/or additionally, the first clinician 150a using a wasting station to waste unused substance from the first patient 160a may trigger the generation of a third transaction record that includes a timestamp, the clinician identifier of the first clinician 150a, a clinician identifier of the second clinician 150b witnessing the wasting, a device identifier of the wasting station, the patient identifier of the first patient 160a, an identifier of the substance being wasted, a quantity of the substance being wasted, and/or the like. As used herein, the "wasting" of a substance may refer to the disposal of a substance in accordance with institutional guidelines and/or government regulations. For example, the proper wasting of a prescription pain medication may require the controlled substance to be collected in a designated receptacle (e.g., wasting stations) while in the presence of one or more witnesses.

It should be appreciated that the one or more data systems 130 may also provide non-transactional data. For instance, the electronic medical record system 135c may store a plurality of electronic medical records (EMRs), each of which including a patient's history including, for example, past opioid use and/or the like. While a timestamp transaction record may be generated as a result of the first clinician 150a and/or the second clinician 150b interacting with the electronic medical record system 135c to create, update, and/or retrieve an electronic medical record for the first patient 160a and/or the second patient 160b, the electronic medical record itself is not a transaction record.

Figure 4:
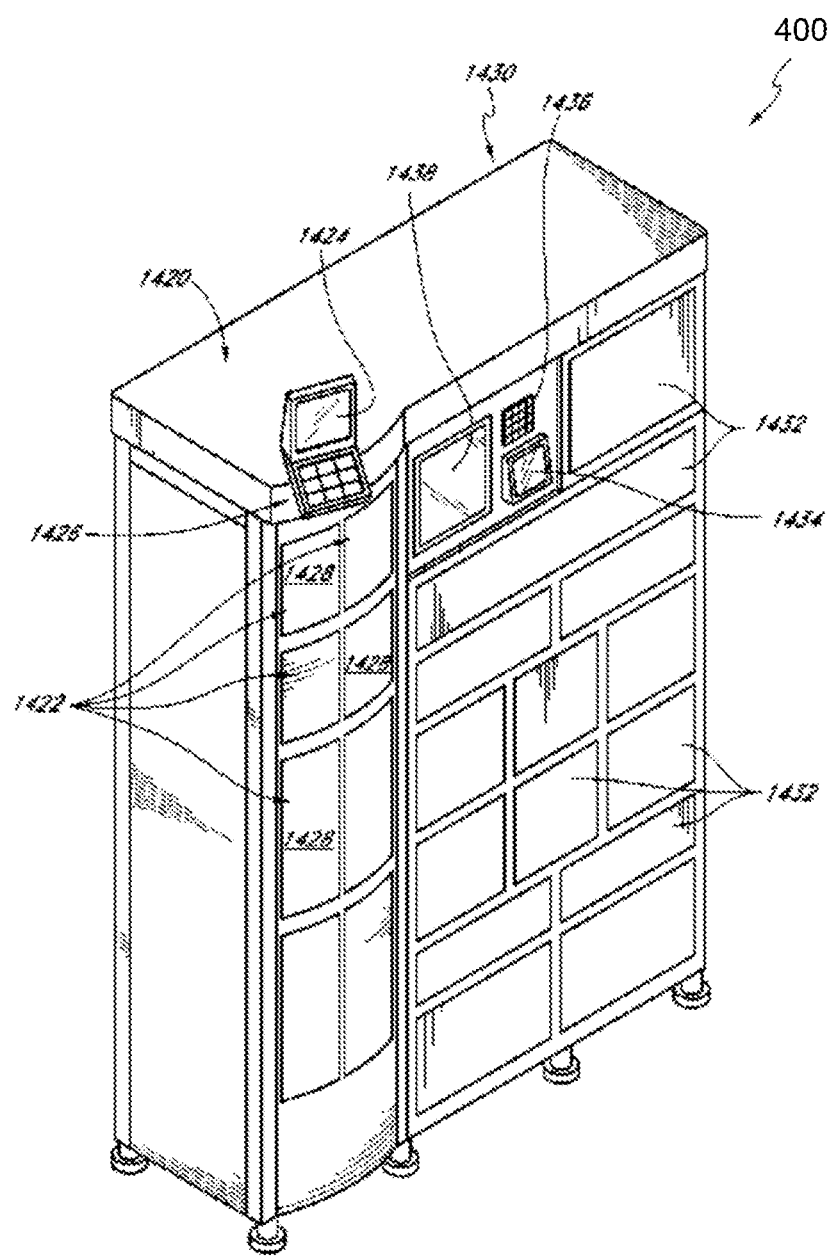
FIG. 4 depicts an example of a medical device, in accordance with some example embodiments.
Figure 5:
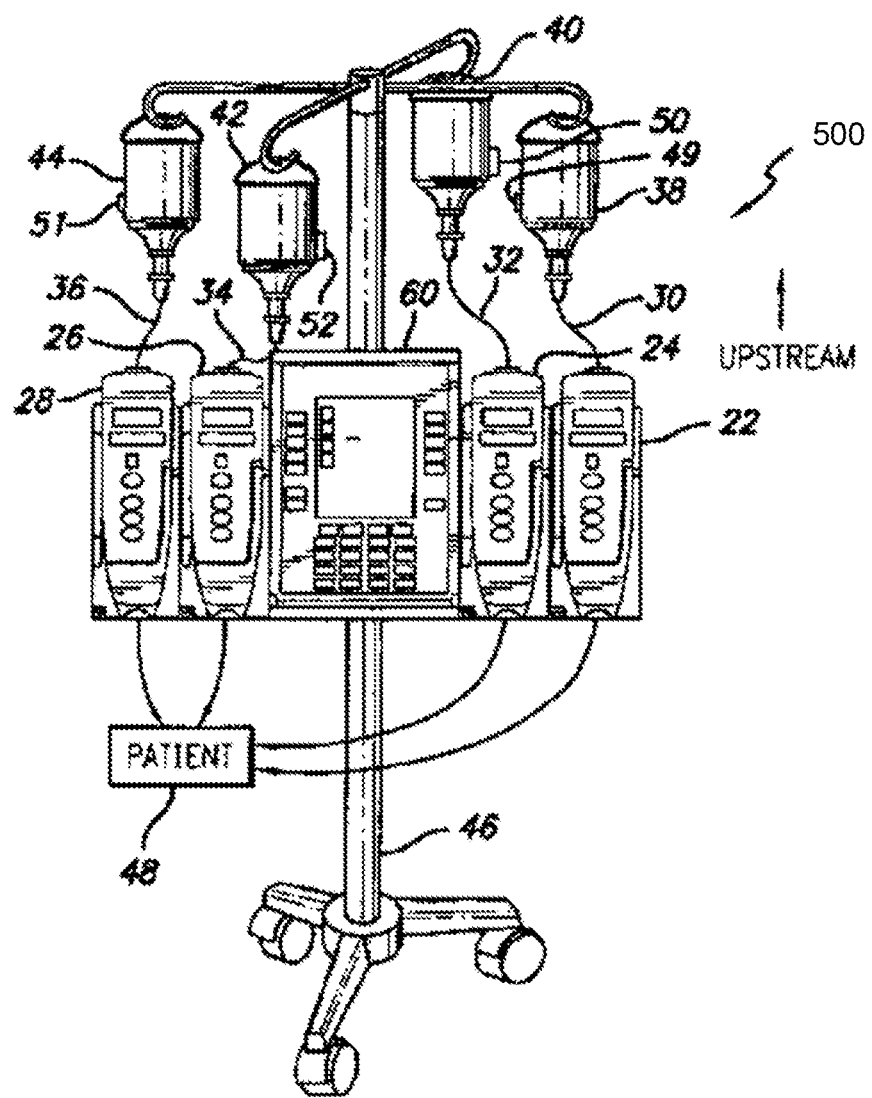
FIG. 5 depicts another example of a medical device, in accordance with some example embodiments.

To further illustrate, FIGS. 4-5 depict examples of medical devices that may be part of the data systems 130. For example, FIG. 4 depicts an example of a dispensing cabinet 400, in accordance with some example embodiments. A clinician dispensing a substance from the dispensing cabinet 400 may trigger the generation of a transaction record that includes a timestamp, a clinician identifier of the clinician, a device identifier of the dispensing cabinet, a patient identifier of a patient prescribed the substance, an identifier of the substance retrieved from the dispensing cabinet, a quantity of the substance retrieved from the substance cabinet, a location identifier, and/or the like. Additional details associated with the dispensing cabinet 400 are described in U.S. Pat. No. 8,195,328, which is commonly owned and hereby incorporated by reference in its entirety.

FIG. 5 depicts an example of an infusion pump 500, in accordance with some example embodiments. A clinician using the infusion pump 500 to administer a substance to a patient may trigger the generation of a transaction record that includes a timestamp, a clinician identifier of the clinician, a device identifier of the infusion pump, a patient identifier of the patient receiving the substance, an identifier of the substance being administered to the patient, a quantity of the substance being administered to the patient, a location identifier, and/or the like. Additional details associated with the infusion pump 500 are described in U.S. Pat. No. 9,227,025, which is commonly owned and hereby incorporated by reference in its entirety.

As noted, the safety controller 110 may identify, based on transaction records from the data systems 130, at least a first shift associated with the first clinician 150a and a second shift associated with the second clinician 150b. As used herein, a shift may refer to a period of time during which a clinician is on duty. It should be appreciated that a single clinician may be associated with different length shifts. Moreover, a single shift may include one or more periods of inactivity (e.g., breaks, meetings, and/or the like) during which a clinician does not generate any transaction records. Accordingly, the safety controller 110 may be unable to correctly identify shifts associated with the first clinician 150a or the second clinician 150b by applying deterministic rules that identifies shifts based on a first transaction record for a day and a last transaction record for the day.

Instead, according to some example embodiments, the safety controller 110 may apply the machine learning model 115, which may be trained to identify, based on transaction records from the one or more data systems 130, at least a first shift associated with the first clinician 150a and second shift associated with the second clinician 150b. For example, the machine learning model 115 may be trained to determine, based at least on the transaction records associated with the first clinician 150a, a start time and/or an end time for at least the first shift associated with the first clinician 150a. Alternatively and/or additionally, the machine learning model 115 may be trained to determine, based at least on the transaction records associated with the second clinician 150b, a start time and/or an end time for at least the second shift associated with the second clinician 150b. The machine learning model 115 may include an input layer for receiving a vector of values representing transaction records. The machine learning model 115 may include an output layer for providing one or more output values identifying shift information. The output values may include likelihood or accuracy values identifying a confidence in a given shift information output. For example, the machine learning model 115 may receive an encoded version of transactions from a previous period of time. The machine learning model 115 output layer may include twenty four output values each representing an hour of a day. Each of the twenty four output values may be associated with a value from 0 to 1 where 0 is a highly unlikely shift boundary and a 1 is a nearly certain shift boundary. The machine learning model 115 may include additional layers to connect the input layer to the output layer. The additional layers may be referred to as hidden layers and include weights that can be trained using historical transaction and shift data to identify shift boundaries for subsequently received transactions.

In some example embodiments, the machine learning model 115 may be a probabilistic machine learning model trained to determine a probability of a clinician being on duty or off duty based on a series of transaction records associated with the clinician. For example, the machine learning model 115 may be a Hidden Markov Model. Moreover, the machine learning model 115 may be trained using a reinforcement learning technique, which trains the machine learning model 115 to maximize a cumulative reward. Examples of reinforcement learning techniques include Q-learning, Monte Carlo, state-action-reward-state-action (SARSA), deep Q network (DQN), deep deterministic policy gradient (DDPG), asynchronous actor-critic algorithm (A3C), trust region policy optimization (TRPO), proximal policy optimization (PPO), and/or the like.

The machine learning model 115 may be defined by tuple (S,A), wherein S may denote a finite set of states $\{(S_1, S_2)\}$ in which a first state $S_1$ corresponds to a clinician being on duty and a second state $S_2$ corresponds to the clinician being off duty. Meanwhile, A may denote a finite set of actions $\{A_1, A_2, \ldots, A_n\}$ that the clinician may perform. That is, the finite set of actions $\{A_1, A_2, \ldots, A_n\}$ may correspond to different types of transaction records from the data systems 130. For example, A may include a first action $A_1$ corresponding to the clinician scanning an access badge at an entry point of a treatment facility, a second action $A_2$ corresponding to the clinician accessing a dispensing cabinet to retrieve a substance, and a third action $A_3$ corresponding to the clinician administering the substance to a patient.

While the clinician is in one of the two states $\{(S_1, S_2)\}$, the clinician performing one of the actions $\{A_1, A_2, \ldots, A_n\}$ may trigger a state transition. For example, while the clinician is in the first state $S_1$ corresponding to the clinician being on duty, the clinician performing one of the actions $\{A_1, A_2, \ldots, A_n\}$ may trigger a state transition to either the first state $S_1$ corresponding to the clinician remaining on duty or the second state $S_2$ corresponding to the clinician being off duty. Alternatively and/or additionally, while the clinician is in the second state $S_2$ corresponding to the clinician being off duty, the clinician performing one of the actions $\{A_1, A_2, \ldots, A_n\}$ may trigger a state transition to either the second state $S_2$ corresponding to the clinician remaining off duty or the first state $S_1$ corresponding to the clinician being on duty. It should be appreciated that a state transition from the second state $S_2$ to the first state $S_1$, which corresponds to the clinician transitioning from being off duty to on duty, may indicate a start of a shift for the clinician. By contrast, a state transition from the second state $S_2$ to the first state $S_1$, which corresponds to the clinician transitioning from being off duty to on duty, may indicate a start of a shift for the clinician.

As noted, the machine learning model 115 may be trained using a reinforcement learning technique. For example, machine learning model 115 may be trained using Q-learning, which is an example of a reinforcement learning technique. The quality Q of a combination of an action performed on a field of the first software application 145B may be expressed as Equation (1) below:

$$Q: S \times A \to \mathbb{R} \tag{1}$$

Prior to commencing the training of the machine learning model 115, the value of Q may be initialized to an arbitrary value. The training of the machine learning model 115 may be an iterative process for updating the value of Q. For example, at each time t, an action $a_t$ may be selected to trigger a transition to a new state $s_{t+1}$, the corresponding reward $r_t$ may be observed, and the value of Q may be updated. The iterative update of the value of Q may be expressed by Equation (2) below:

$$Q^{new}(s_t, a_t) \leftarrow (1-\alpha) \cdot Q(s_t, a_t) + \alpha \cdot \left( r_t + \gamma \cdot \max_a Q(s_{t+1}, a) \right) \tag{2}$$

wherein $r_t$ may denote a reward observed for the current state $s_t$, a may denote a learning rate (e.g., 0<a<1), γ may denote the discount factor, $Q(s_t, a_t)$ may denote a value of Q from a previous iteration, and $$\max_a Q(s_{t+1}, a)$$

may correspond to an estimated optimal future value of Q. Referring to Equation (2), it should be appreciated that the r $$\left( r_t + \gamma \cdot \max_a Q(s_{t+1}, a) \right)$$

may correspond to a learned value. Meanwhile, the reward $r_t$ may correspond to a cumulative reward associated with all state transitions up to time t.

In some example embodiments, the machine learning model 115 may be trained based on training data that includes series of transaction records forming ground truth shifts. For example, the ground truth shifts may be actual shifts associated with the first clinician 150a and/or the second clinician 150b. Alternatively and/or additionally, the ground truth shifts may be synthesized based actual shifts associated with the first clinician 150a and/or the second clinician 150b as well as additional data including, for example, medical protocol, generalized observations, and/or the like.

In some example embodiments, the training of the machine learning model 115 may be performed offline and/or in real time. For example, the safety controller 110 may detect a discrepancy between the output of the machine learning model 115 and the transaction records received from the data systems 130. Examples of discrepancies may include the data systems 130 generating a transaction record that is inconsistent with an output of the machine learning model 115 indicating a start or an end of a shift associated with the first clinician 150a and/or the second clinician 150b. The safety controller 110 may respond to the discrepancy by at least triggering a retraining of the machine learning model 115. For instance, the machine learning model 115 may be retrained, either offline or in real time, based on additional training data including ground truth shifts adjusted to include the transaction record. In instances where the safety controller 110 is at least partially embedded and/or implemented within the one or more data systems 130, the retrained machine learning model 115 may be propagated to the one or more data systems 130 (e.g., the access control system 135a, the dispensing system 135b, the electronic medical record (EMR) system 135c, and/or the like) as part of a routine servicing and/or software update at the one or more data systems 130.

In some example embodiments, the safety controller 110 may be configured to detect, based on one or more shifts associated with the first clinician 150a and/or the second clinician 150b, one or more high risk periods during which the first clinician 150a and/or the second clinician 150b are likely to engage in hazardous behavior including, for example, the diversion and/or mishandling of substance. Examples of high risk periods may include shift changes (e.g., a n-quantity of time prior to an end of a shift and/or an n-quantity of time subsequent to a start of a shift), portions of shifts exceeding a threshold quantity of time, and/or the like. The safety controller 110 may be configured to activate a protective workflow in response to detecting the one or more high risk periods. For example, the safety controller 110 may activate the protective workflow during the one or more high risk periods.

The protective workflow may be configured to prevent the first clinician 150a and/or the second clinician 150b from engaging in the hazardous behavior during the high risk periods. For example, the protective workflow may include the safety controller 110 generating and sending, to the client 120 associated with a facility supervisor, one or more electronic alerts (e.g., an email, a push notification, a short messaging service (SMS) message, and/or the like) identifying the first clinician 150a and/or the second clinician 150b as likely to engage in hazardous behavior during the high risk periods.

Alternatively and/or additionally, the protective workflow may include preventing the first clinician 150a and/or the second clinician 150b from performing certain activities (e.g., retrieving, administering, and/or wasting certain substances) during the high risk periods. For instance, the protective workflow may include the safety controller 110 configuring one or more medical devices (e.g., dispensing cabinet, infusion pump, wasting station, and/or the like) to limit and/or deny interactions with certain substances. The safety controller 110 may configure a medical device to prevent the first clinician 150a and/or the second clinician 150b from retrieving and/or administering certain substances without authorization from a third clinician 150c. For example, as part of the protective workflow, a dispensing cabinet may be configured to prevent the first clinician 150a and/or the second clinician 150b from accessing receptacles holding prescription pain medication without authorization from the third clinician 150c.

In some example embodiments, the protective workflow may be configured to collect evidence of hazardous behavior. For example, the protective workflow may include the safety controller 110 activating one or more surveillance devices (e.g., video cameras, still image cameras, audio recorders, and/or the like) at a medical device (e.g., dispensing cabinet, infusion pump, wasting station, and/or the like) whenever the first clinician 150a and/or the second clinician 150b access the medical device. Alternatively and/or additionally, the protective workflow may include the safety controller 110 configuring a medical device to isolate the substance accessed by the first clinician 150*a* and/or the second clinician 150*b*.

In some example embodiments, the safety controller 110 may also be configured to identify the first clinician 150*a* as likely to have engaged in hazardous behavior by at least comparing a first shift associated with the first clinician 150*a* to at least a second shift associated with the first clinician 150*a* and/or a third shift the second clinician 150*b*. It should be appreciated that the safety controller 110 may compare two or more shifts selectively. That is, the safety controller 110 may compare two or more shifts that are similar by having one or more common attributes including, for example, duration, time of day, facility, department, patient, and/or the like. Moreover, the safety controller 110 may compare shifts associated with different clinicians having the same and/or similar user types including, for example, physician, pharmacy technician, nurse manager, nurse practitioner, and/or the like.

The safety controller 110 may detect the occurrence of hazardous behavior occurred during the first shift associated with the first clinician 150*a* by at least comparing the transaction records included in the first shift associated with the first clinician 150*a* against the transaction records included in the second shift associated with the first clinician 150*a* and/or the third shift associated with the second clinician 150*b*. In doing so, the safety controller 110 may detect the presence of one or more anomalies including one or more anomalous transaction records. The presence of anomalies in the first shift associated with the first clinician 150*a* may indicate that the first clinician 150*a* has engaged in hazardous behavior including, for example, the diversion and/or mishandling of a substance.

The safety controller 110 may activate a protective workflow in response to identifying the first clinician 150*a* as likely to have engaged in the hazardous behavior. In some example embodiments, the protective workflow may be configured to prevent future occurrences of the hazardous behavior and/or to collect evidence associated with the hazardous behavior. For example, the protective workflow may include the safety controller 110 generating and sending one or more electronic alerts (e.g., an email, a push notification, a short messaging service (SMS) message, and/or the like) identifying the first clinician 150*a* as likely to have engaged in hazardous behavior. The one or more electronic alerts may be sent to the client 120 associated with a facility supervisor.

In some example embodiments, the protective workflow may further include safety controller 110 activating one or more surveillance devices (e.g., video cameras, still image cameras, audio recorders, and/or the like) at a medical device (e.g., dispensing cabinet, infusion pump, wasting station, and/or the like) whenever the first clinician 150*a* accesses the medical device. Alternatively and/or additionally, the safety controller 110 may configure the medical device to isolate substance accessed by the first clinician 150*a*. For example, the safety controller 110 may activate a surveillance device at a wasting station in response to the first clinician 150*a* accessing the wasting station to dispose of unused substance. Moreover, the safety controller 110 may configure the wasting station to isolate the unused substance returned by the first clinician 150*a*, for example, in a designated receptacle that is separate from the receptacles holding unused substance returned by other clinicians.

Figure 2A:
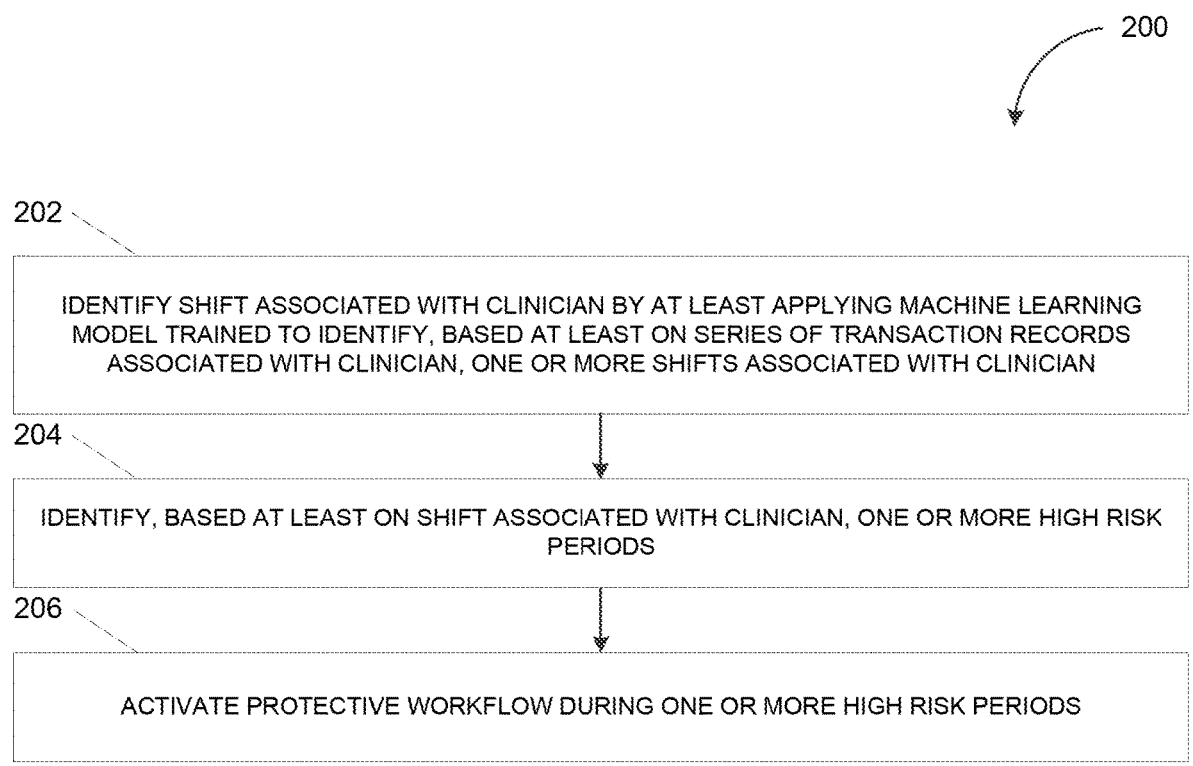
FIG. 2A depicts a flowchart illustrating an example of a process for machine learning based safety controls, in accordance with some example embodiments.

FIG. 2A depicts a flowchart illustrating another example of a process 200 for machine learning based safety controls, in accordance with some example embodiments. Referring to FIGS. 1 and 2A, the process 200 may be performed by the safety control system 100, for example, by the safety controller 110.

At 202, the safety controller 110 may identify a shift associated with a clinician by at least applying a machine learning model trained to identify, based at least on a series of transaction records associated with the clinician, one or more shifts associated with the first clinician. For example, the safety controller 110 may apply the machine learning model 115 in order to identify one or more shifts associated with the first clinician 150*a*. As noted, the machine learning model 115 may be trained to identify the one or more shifts associated with the first clinician 150*a* based at least on a series of transaction records associated with the first clinician 150*a*.

In some example embodiments, each transaction record in the series of transaction records may be generated in response to the first clinician 150*a* interacting with one or more data systems 130, which may include, for example, the access control system 135*a*, the dispensing system 135*b*, and/or the electronic medical record system 135*c*. For instance, a first transaction record may be generated in response to the first clinician 150*a* interacting with the access control system 135*a* by scanning an access badge at an entry point in a treatment facility. Meanwhile, a second transaction record may be generated in response to the first clinician 150*a* interacting with the dispensing system 135*b* to retrieve, administer, and/or waste a substance. Alternatively and/or additionally, a third transaction record may be generated in response to the first clinician 150*a* interacting with the electronic medical record (EMR) system 135*c* when administering the substance to a patient. Accordingly, the machine learning model 115 may be trained to recognize one or more transaction records indicative of the first clinician 150*a* being at a start of a shift and/or an end of the shift.

At 204, the safety controller 110 may identify, based at least on the shift associated with the clinician, one or more high risk periods. For example, the safety controller 101 may identify, based at least on the shift associated with the first clinician 150*a*, one or more high risk periods during which the first clinician 150*a* is likely to engage in hazardous behavior such as, for example, diversion and/or mishandling of a substance. Examples of high risk periods may include a shift change (e.g., a n-quantity of time prior to an end of a shift and/or an n-quantity of time subsequent to a start of a shift), portions of shifts exceeding a threshold quantity of time, and/or the like.

At 206, the safety controller 110 may activate a protective workflow during the one or more high risk periods. In some example embodiments, the safety controller 110 may activate a protective workflow configured to prevent the first clinician 150*a* from engaging in the hazardous behavior during the high risk periods and/or collect evidence associated with the hazardous behavior. For example, the protective workflow may include the safety controller 110 generating and sending, to the client 120 associated with a facility supervisor, one or more electronic alerts (e.g., an email, a push notification, a short messaging service (SMS) message, and/or the like) identifying the first clinician 150*a* as likely to engage in hazardous behavior during the high risk periods. The protective workflow may also include the safety controller 110 configuring one or more medical devices (e.g., dispensing cabinet, infusion pump, wasting station, and/or the like) to limit and/or deny interactions with certain substances. For instance, the safety controller 110 may configure a medical device to prevent the first clinician 150*a* from retrieving and/or administering certain substances without additional authorization (e.g., from the third clinician 150c).

Alternatively and/or additionally, the protective workflow may include the safety controller 110 activating one or more surveillance devices (e.g., video cameras, still image cameras, audio recorders, and/or the like) at a medical device (e.g., dispensing cabinet, infusion pump, wasting station, and/or the like) whenever the first clinician 150a accesses the medical device. The protective workflow may also include the safety controller 110 configuring a medical device to isolate the substance accessed by the first clinician 150a.

Figure 2B:
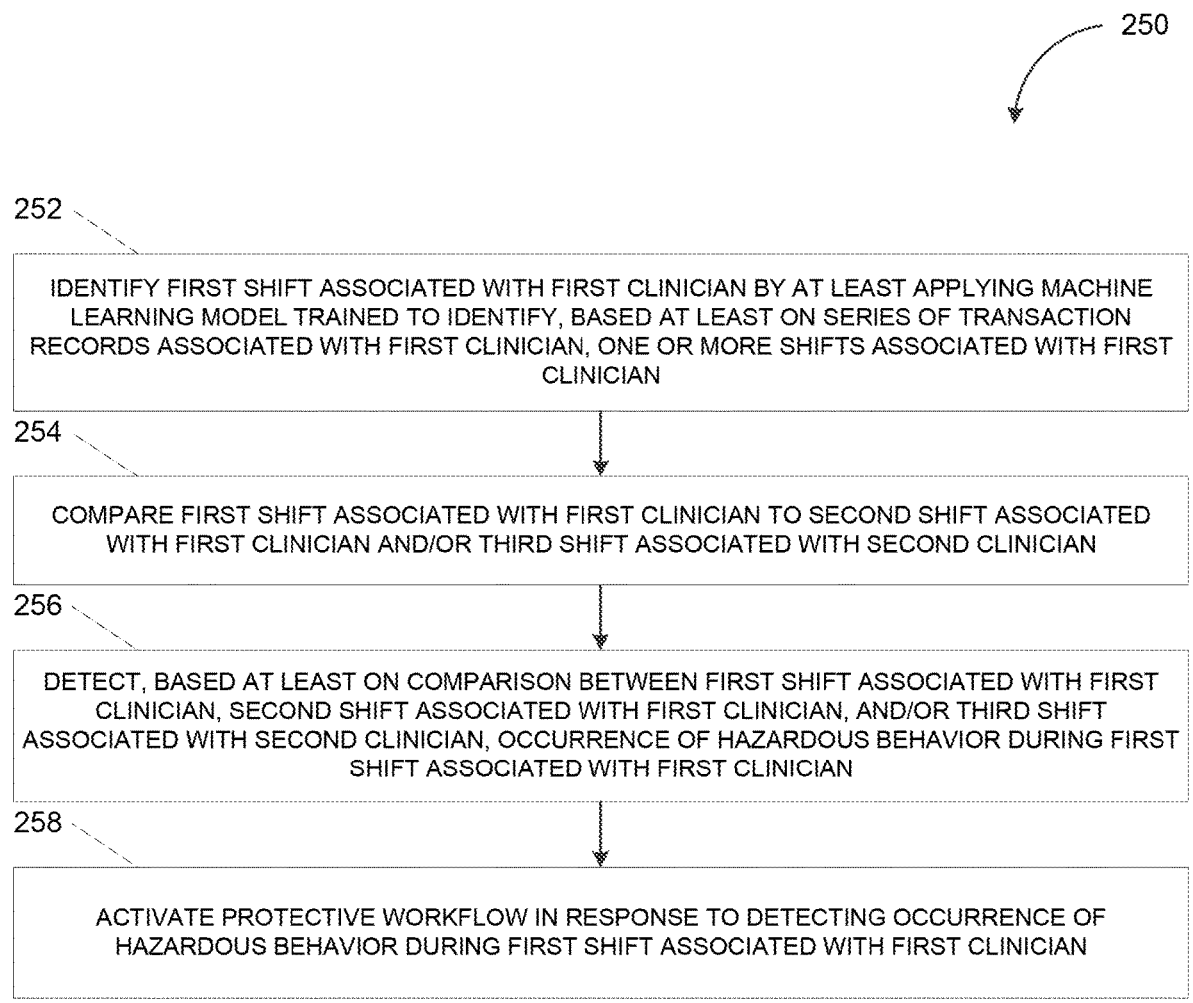
FIG. 2B depicts a flowchart illustrating another example of a process for machine learning based safety controls, in accordance with some example embodiments.

FIG. 2B depicts a flowchart illustrating another example of a process 250 for machine learning based safety controls, in accordance with some example embodiments. Referring to FIGS. 1 and 2B, the process 250 may be performed by the safety control system 100, for example, by the safety controller 110.

At 252, the safety controller 110 may identify a first shift associated with a first clinician by at least applying a machine learning model trained to identify, based at least on a series of transaction records associated with the first clinician, one or more shifts associated with the first clinician. In some example embodiments, the safety controller 110 may apply the machine learning model 115 in order to identify one or more shifts associated with the first clinician 150a. As noted, the machine learning model 115 may be trained to identify the one or more shifts associated with the first clinician 150a based at least on a series of transaction records associated with the first clinician 150a.

At 254, the safety controller 110 may compare the first shift associated with the first clinician to a second shift associated with the first clinician and/or a third shift associated with a second clinician. For example, the safety controller 110 may compare the transaction records included in the first shift associated with the first clinician 150a against the transaction records included in the second shift associated with the first clinician 150a and/or the third shift associated with the second clinician 150b. As noted, the safety controller 110 may detect the occurrence of anomalous behavior in a shift by at least comparing the shift to similar shifts associated with the same clinician and/or different clinician. Accordingly, the first shift associated with the first clinician 150a, the second shift associated with the first clinician 150a, and/or the third shift associated with the second clinician 150b may share at least one common attribute including, for example, duration, time of day, facility, department, patient, and/or the like.

At 256, the safety controller 110 may detect, based at least on the comparison (e.g., from 204) between the first shift associated with the first clinician, the second shift associated with the first clinician, and/or the third shift associated with the second clinician, an occurrence of anomalous behavior during the first shift associated with the first clinician. In some example embodiments, the safety controller 110 may compare the transaction records included in the first shift associated with the first clinician 150a against the transaction records included in the second shift associated with the first clinician 150a and/or the third shift associated with the second clinician 150b in order to identify one or more anomalous transaction records. An anomalous transaction may be a transaction that appears in one shift but not the other shift. An anomalous transaction may be a transaction that appears at a given time in one shift and at a different time in the other shift. An anomalous transaction may be identified using aggregations. For example, in a typical shift, the clinician may perform a type of transaction (e.g., request for substance dispensing) ten times but during a different shift, the type of transaction may appear more or less frequently. An anomaly may be specified using a threshold to permit small differences between transaction attributes (e.g., differences in transaction time or dispensing requests), but flag differences which exceed the threshold. The presence of one or more anomalous transaction records in the first shift associated with the first clinician 150a may indicate that the first clinician 150a has engaged in hazardous behavior including, for example, the diversion and/or mishandling of a substance.

At 258, the safety controller 110 may activate a protective workflow in response to detecting the occurrence of anomalous behavior during the first shift associated with the first clinician. For example, the safety controller 110 may determine that the first clinician 150a is likely to have engaged in hazardous behavior such as the diversion and/or mishandling of a substance. Accordingly, the safety controller 110 may activate a protective workflow configured to prevent future occurrences of the hazardous behavior and/or collect evidence associated with the hazardous behavior. For instance, the protective workflow may include the safety controller 110 generating an electronic alert that includes, for example, a wireless alert message such as, for example, a push notification, a short messaging service (SMS) message, and/or the like. The electronic alert may be sent to the client 120, which may be associated with a supervisor associated with the first clinician 150a.

In some example embodiments, the protective workflow may also include the safety controller 110 configuring one or more medical devices (e.g., dispensing cabinet, infusion pump, wasting station, and/or the like) to limit and/or deny interactions with certain substances such as, for example, prescription medications, high value medical supplies, and/or the like. For instance, the safety controller 110 may configure a medical device to prevent the first clinician 150a from retrieving and/or administering certain substances without additional authorization (e.g., from the third clinician 150c).

Alternatively and/or additionally, the protective workflow may include the safety controller 110 activating one or more surveillance devices (e.g., video cameras, still image cameras, audio recorders, and/or the like) at a medical device (e.g., dispensing cabinet, infusion pump, wasting station, and/or the like) whenever the first clinician 150a accesses the medical device. The protective workflow may also include the safety controller 110 configuring a medical device to isolate the substance accessed by the first clinician 150a.

Figure 3:
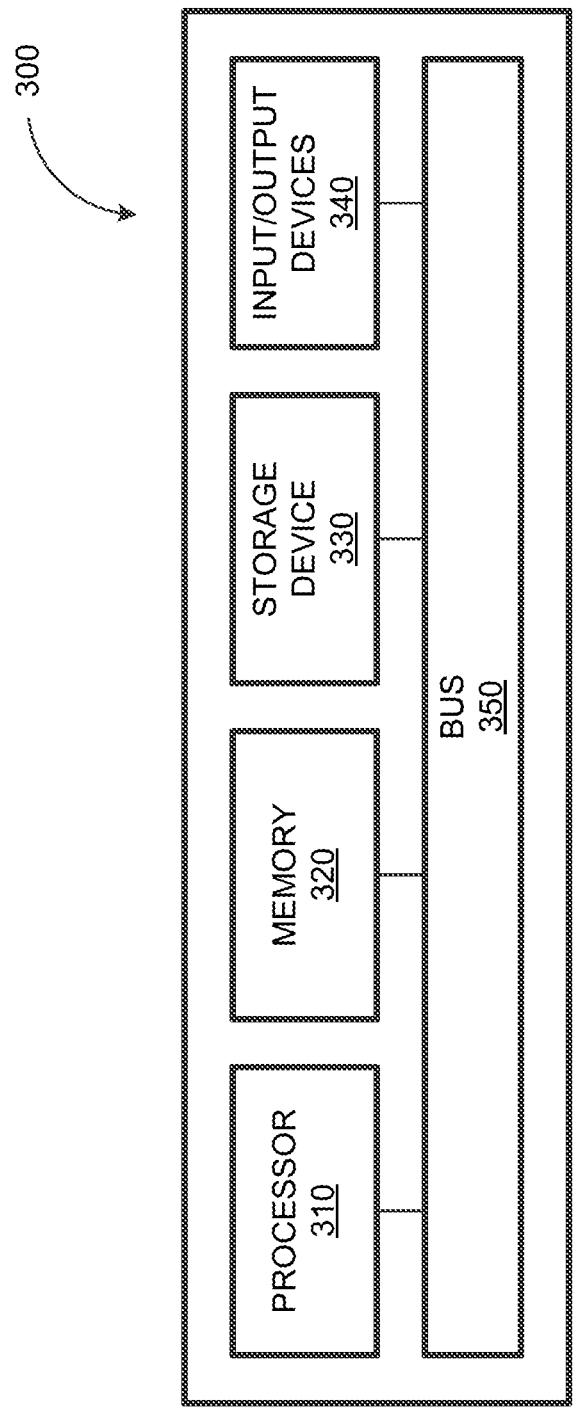
FIG. 3 depicts a block diagram illustrating a computing system, in accordance with some example embodiments.

FIG. 3 depicts a block diagram illustrating a computing system 300 consistent with implementations of the current subject matter. Referring to FIGS. 1 and 2, the computing system 300 can be used to implement the safety controller 110 and/or any components therein.

As shown in FIG. 3, the computing system 300 can include a processor 310, a memory 320, a storage device 330, and input/output device 340. The processor 310, the memory 320, the storage device 330, and the input/output device 340 can be interconnected via a system bus 350. The processor 310 is capable of processing instructions for execution within the computing system 300. Such executed instructions can implement one or more components of, for example, the safety controller 110. In some example embodiments, the processor 310 can be a single-threaded processor. Alternatively, the processor 310 can be a multi-threaded processor. The processor 310 is capable of processing instructions stored in the memory 320 and/or on the storage device 330 to display graphical information for a user interface provided via the input/output device 340.

The memory 320 is a computer readable medium such as volatile or non-volatile that stores information within the computing system 300. The memory 320 can store data structures representing configuration object databases, for example. The storage device 330 is capable of providing persistent storage for the computing system 300. The storage device 330 can be a floppy disk device, a hard disk device, an optical disk device, a tape device, a solid-state device, and/or any other suitable persistent storage means. The input/output device 340 provides input/output operations for the computing system 300. In some example embodiments, the input/output device 340 includes a keyboard and/or pointing device. In various implementations, the input/output device 340 includes a display unit for displaying graphical user interfaces.

According to some example embodiments, the input/output device 340 can provide input/output operations for a network device. For example, the input/output device 340 can include Ethernet ports or other networking ports to communicate with one or more wired and/or wireless networks (e.g., a local area network (LAN), a wide area network (WAN), the Internet).

In some example embodiments, the computing system 300 can be used to execute various interactive computer software applications that can be used for organization, analysis and/or storage of data in various formats. Alternatively, the computing system 300 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 340. The user interface can be generated and presented to a user by the computing system 300 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data can be forwarded to a "remote" device or location," where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

One or more aspects of the artificial intelligence described may be implemented in whole or in part by a model. A model may be implemented as a machine learning model. The learning may be supervised, unsupervised, reinforced, or a hybrid learning whereby multiple learning techniques are employed to generate the model. The learning may be performed as part of training. Training the model may include obtaining a set of training data and adjusting characteristics of the model to obtain a desired model output. For example, three characteristics may be associated with a desired device state. In such instance, the training may include receiving the three characteristics as inputs to the model and adjusting the characteristics of the model such that for each set of three characteristics, the output device state matches the desired device state associated with the historical data.

In some implementations, the training may be dynamic. For example, the system may update the model using a set of events. The detectable properties from the events may be used to adjust the model.

The model may be an equation, artificial neural network, recurrent neural network, convolutional neural network, decision tree, or other machine readable artificial intelligence structure. The characteristics of the structure available for adjusting during training may vary based on the model selected. For example, if a neural network is the selected model, characteristics may include input elements, network layers, node density, node activation thresholds, weights between nodes, input or output value weights, or the like. If the model is implemented as an equation (e.g., regression), the characteristics may include weights for the input parameters, thresholds or limits for evaluating an output value, or criterion for selecting from a set of equations.

Once a model is trained, retraining may be included to refine or update the model to reflect additional data or specific operational conditions. The retraining may be based on one or more signals detected by a device described herein or as part of a method described herein. Upon detection of the designated signals, the system may activate a training process to adjust the model as described.

Further examples of machine learning and modeling features which may be included in the embodiments discussed above are described in "A survey of machine learning for big data processing" by Qiu et al. in EURASIP Journal on Advances in Signal Processing (2016) which is hereby incorporated by reference in its entirety.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device, diagnostic device, monitoring device, or server in communication therewith.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:
    at least one data processor; and
    at least one memory storing instructions which, when executed by the at least one data processor, result in operations comprising:
        identifying a first shift associated with a first clinician by at least applying a machine learning model trained to identify, based at least on a series of transaction records associated with the first clinician, one or more shifts associated with the first clinician, the machine learning model having an on-duty state and an off-duty state, and the machine learning model identifying the first shift by at least determining, for each successive transaction record in the series of transaction records, a probability of the first clinician being on-duty or off-duty, and determining, based at least on the probability of the first clinician being on-duty or off-duty, whether to remain in a same state or to transition between the on-duty state and the off-duty state;
        determining, based at least on the first shift associated with the first clinician, that the first clinician is a candidate for engaging in a hazardous behavior; and
        in response to determining that the first clinician is the candidate for engaging in the hazardous behavior, configuring a wasting station to open a designated receptacle to receive as waste an unused substance, the designated receptacle isolating the unused substance returned by the first clinician in the designated receptacle that is separate from receptacles holding unused substance returned by other clinicians.

2. The system of claim 1, wherein the operations further comprise:
    comparing the first shift associated with the first clinician to a second shift associated with the first clinician and/or a third shift associated with a second clinician; and
    determining, based at least on the comparing, that the first clinician is likely to engage in the hazardous behavior.

3. The system of claim 2, wherein the first shift associated with the first clinician is compared to the second shift associated with the first clinician and/or the third shift associated with the second clinician by at least comparing a first plurality of transaction records included in the first shift to a second plurality of transaction records included in the second shift and/or the third shift.

4. The system of claim 3, wherein the first clinician is determined to be likely to engage in the hazardous behavior in response to detecting one or more anomalous transaction records included in the first plurality of transaction records.

5. The system of claim 2, wherein the first shift associated with the first clinician is compared to the second shift associated with the first clinician and/or the third shift associated with the second clinician based at least on the first shift having one or more attributes in common with the second shift and/or the third shift.

6. The system of claim 2, wherein the first shift associated with the first clinician is compared to the third shift associated with the second clinician based at least on the first clinician and the second clinician having one or more attributes in common.

7. The system of claim 1, wherein the operations further comprise:
    identifying, based at least on the first shift associated with the first clinician, one or more high risk periods during which the first clinician is likely to engage in the hazardous behavior; and
    activating a protective workflow during the one or more high risk periods.

8. The system of claim 7, wherein the one or more high risk periods include at least one of a first quantity of time subsequent to a start of the first shift and a second quantity of time prior to an end of the first shift.

9. The system of claim 7, wherein the one or more high risk periods include a portion of the first shift exceeding a threshold quantity of time.

10. The system of claim 1, wherein the machine learning model is a probabilistic machine learning model.

11. The system of claim 10, wherein the machine learning model transitions from the off-duty state to the on-duty state to indicate a start of the first shift associated with the first clinician, and wherein the machine learning model transitions from the on-duty state to the off-duty state to indicate an end of the first shift associated with the first clinician.

12. The system of claim 10, wherein the probabilistic machine learning model is trained using a reinforcement learning technique comprising Q-learning, Monte Carlo, state-action-reward-state-action (SARSA), deep Q network (DQN), deep deterministic policy gradient (DDPG), asynchronous actor-critic algorithm (A3C), trust region policy optimization (TRPO), and/or proximal policy optimization (PPO).

13. The system of claim 1, wherein the series of transaction records includes one or more transaction records generated in response to the first clinician interacting with an access control system, and wherein a transaction record indicates scanning, via the access control system, an access badge at an entry point of a treatment facility.

14. The system of claim 1, wherein the series of transaction records includes one or more transaction records generated in response to the first clinician interacting with a dispensing system, and wherein a transaction record indicates accessing a dispensing cabinet associated with the dispensing system to retrieve a substance.

15. The system of claim 1, wherein the series of transaction records includes one or more transaction records generated in response to the first clinician interacting with an electronic medical record (EMR) system, and wherein a transaction record indicates administration of a substance to a patient identified in the EMR system.

16. The system of claim 1, wherein the operations further comprise:
in response to determining that the first clinician is the candidate for engaging in the hazardous behavior, generating an alert identifying the first clinician as likely to engage in the hazardous behavior.

17. The system of claim 1, wherein the operations further comprise:
in response to determining that the first clinician is the candidate for engaging in the hazardous behavior, activating one or more surveillance devices in response to the first clinician interacting with a medical device.

18. The system of claim 1, wherein the operations further comprise:
in response to determining that the first clinician is the candidate for engaging in the hazardous behavior, configuring one or more medical devices to prevent the first clinician from retrieving, administering, and/or wasting a substance without supervision and/or authorization from a second clinician.

19. A computer-implemented method, comprising:
identifying a first shift associated with a first clinician by at least applying a machine learning model trained to identify, based at least on a series of transaction records associated with the first clinician, one or more shifts associated with the first clinician, the machine learning model having an on-duty state and an off-duty state, and the machine learning model identifying the first shift by at least determining, for each successive transaction record in the series of transaction records, a probability of the first clinician being on-duty or off-duty, and determining, based at least on the probability of the first clinician being on-duty or off-duty, whether to remain in a same state or to transition between the on-duty state and the off-duty state;
determining, based at least on the first shift associated with the first clinician, that the first clinician is a candidate for engaging in a hazardous behavior; and
in response to determining that the first clinician is the candidate for engaging in the hazardous behavior, configuring a wasting station to open a designated receptacle to receive as waste an unused substance, the designated receptacle isolating the unused substance returned by the first clinician in the designated receptacle that is separate from receptacles holding unused substance returned by other clinicians.

20. A non-transitory computer readable medium storing instructions, which when executed by at least one data processor, result in operations comprising:
identifying a first shift associated with a first clinician by at least applying a machine learning model trained to identify, based at least on a series of transaction records associated with the first clinician, one or more shifts associated with the first clinician, the machine learning model having an on-duty state and an off-duty state, and the machine learning model identifying the first shift by at least determining, for each successive transaction record in the series of transaction records, a probability of the first clinician being on-duty or off-duty, and determining, based at least on the probability of the first clinician being on-duty or off-duty, whether to remain in a same state or to transition between the on-duty state and the off-duty state;
determining, based at least on the first shift associated with the first clinician, that the first clinician is a candidate for engaging in a hazardous behavior; and
in response to determining that the first clinician is the candidate for engaging in the hazardous behavior, configuring a wasting station to open a designated receptacle to receive as waste an unused substance, the designated receptacle isolating the unused substance returned by the first clinician in the designated receptacle that is separate from receptacles holding unused substance returned by other clinicians.

* * * * *